US008217355B1

(12) United States Patent
Wong

(10) Patent No.: US 8,217,355 B1
(45) Date of Patent: Jul. 10, 2012

(54) SELF-COMMISSIONING NDIR GAS SENSORS

(75) Inventor: Jacob Y Wong, Goleta, CA (US)

(73) Assignee: Airware, Inc., Goleta, CA (US)

( * ) Notice: Subject to any disclaimer, the term of this patent is extended or adjusted under 35 U.S.C. 154(b) by 0 days.

(21) Appl. No.: 13/420,323

(22) Filed: Mar. 14, 2012

Related U.S. Application Data

(63) Continuation-in-part of application No. 13/149,738, filed on May 31, 2011, now Pat. No. 8,178,832.

(51) Int. Cl.
*G01J 5/02* (2006.01)
*G01J 5/00* (2006.01)

(52) U.S. Cl. ....... 250/345; 250/252.1; 73/1.02; 73/1.03; 73/31.02; 356/437

(58) Field of Classification Search .................. 250/345, 250/338.5, 343, 344, 252.1, 573, 346; 422/83; 702/85; 356/437, 440, 432, 436, 246, 433; 73/31.02, 21.2, 23.21, 23.22, 1.02, 1.03
See application file for complete search history.

(56) References Cited

U.S. PATENT DOCUMENTS

| | | | | |
|---|---|---|---|---|
| 3,560,736 A | * | 2/1971 | Billetdeaux et al. | 250/343 |
| 3,725,701 A | * | 4/1973 | Link | 250/343 |
| 8,143,581 B2 | * | 3/2012 | Wong | 250/345 |
| 2011/0090505 A1 | * | 4/2011 | Kuze et al. | 356/437 |

* cited by examiner

*Primary Examiner* — David Porta
*Assistant Examiner* — Yara Green
(74) *Attorney, Agent, or Firm* — Roy L Anderson; Wagner, Anderson & Bright, P.C.

(57) ABSTRACT

Two detectors of the same kind, each having an identical neutral band-pass filter to the target gas, are installed next to Signal channel and Reference channel detectors as pairs in an AB designed NDIR gas sensor layout, which are called Standard Signal channel detector and Standard Reference channel detector. "Standard" GAMMA is the ratio of Standard signal channel detector output over that of Standard Reference channel detector. "Standard" GAMMA is independent of the measurement Physics of NDIR gas sensors, is dependent only upon the performance characteristics of the sensor component and is also independent of the presence of any amount of target gas in the sample chamber. Consequently, "Standard" GAMMA can be used to proportionally correct and update GAMMA of the sensor as its components age over time thereby rendering such an AB designed NDIR gas sensor self-commissioning or staying accurate over time after initial calibration.

20 Claims, 2 Drawing Sheets

SELF-COMMISSIONING NDIR GAS SENSORS

CROSS REFERENCE TO RELATED APPLICATIONS

This application is a continuation-in-part application of U.S. patent application Ser. No. 13/149,738, the disclosure of which is specifically incorporated herein by reference.

FIELD OF THE INVENTION

The present invention is in the field of measuring instruments, and specifically relates to a configuration design and method for an NDIR gas sensor.

BACKGROUND OF THE INVENTION

Output instability or drift over time leading to measurement inaccuracies has long been a major deficiency for gas sensors irrespective of what technology or methodology is used for their conception or realization. Output software correction may alleviate the problem somewhat but it is in many instances inaccurate and not even always applicable. It has long been the objective of many researchers in this field to overcome this problem fundamentally and for good.

Recently the present author in U.S. Pat. No. 8,143,581, the disclosure of which is specifically incorporated by reference herein, advanced the teaching of an Absorption Biased NDIR Gas Sensing Methodology which is capable of eliminating substantially all the NDIR gas sensor output drifts over time without the need for re-calibration. As it turns out, the solution to solving this output drift problems for gas sensors actually lies deeper than the availability of superior NDIR gas sensor types even though they can indeed be designed to be capable of maintaining measurement accuracy over time. The fact of the matter is that people have experienced gas sensor output instability for such a long time in the past that when output stable sensors really come along nobody believes it. Until such time that stable gas sensors become widely available and users begin to consider their performance as trustworthy and truly believable, the real need today must be viewed from a completely different perspective, which is to be able to come up with a fast, inexpensive and simple methodology that can easily check the accuracy of gas sensors and inexpensively re-calibrate them when they are found to be inaccurate.

In U.S. application Ser. No. 13/149,738, filed May 31, 2011, of which this application is a continuation-in-part application, the present author advanced the teaching of a novel Re-calibration Methodology for simply and easily re-calibrating Absorption Biased (AB) designed NDIR gas sensors without the need of standard gases. With the recent advent of the Absorption Biased (AB) gas sensing methodology for realizing NDIR gas sensors whose outputs are significantly drift-free over time and also the advent of a complementing methodology that can check and re-calibrate AB designed NDIR gas sensors simply and easily without the need of standard gases, one would think that the gas sensor industry at large, particularly the HVAC industry, would be relatively satisfied and happily go forward in growing its business. But, unfortunately, this is not the case at all. While the HVAC industry is still trying to deal with their old and on-going problem of sensor inaccuracies over time, already the industry is pushing forward in finding new and better solutions for optimizing energy expenditure and achieving superior comfort level for occupants in buildings. One rather obvious approach widely being investigated and considered everywhere today is the grouping of all sensors in a building together into a computer network. These sensors can actually interact and work with one another in an efficient manner with self-commissioning, self-tuning, self-diagnostic and correction, and even self-configuring features. By so doing the energy requirement for buildings can be reduced to an absolute minimum while the comfort level and safety for occupants in the buildings can also be greatly increased.

No doubt from the standpoint of computer networking hardware and smart software availability today, this approach is clearly workable. However, when all the sensors are to be left alone by themselves to interact with one another over time in buildings, the obvious question to ask is whether these sensors are indeed ready to take on this self-policing task of always staying accurate. In other words, who is there to check whether the outputs of some of these sensors are actually staying accurate over time and if not, what are the consequences for the maintenance status of the buildings and the comfort level and safety of their occupants? Thus, while computer hardware and system networking software may be ready for this futuristic approach to building controls, it is very clear that not all the sensors needed to perform perfectly in this approach are here today to meet the challenge. In particular, gas sensors such as $CO_2$ and dew point might be relatively accurate over time but for how long before they become inaccurate? But would there be anybody or any mechanism scheduled in the networking controls system to perform the checking or re-calibrating tasks for them? To put it bluntly, until such time that all the required sensors in the networking controls system can be self-commissioning or in other words can render themselves capable of automatically staying accurate all the time, the futuristic building controls approach with the use of computer networking and relevant software to connect all the sensors in the system together working interactively simply will not work.

It is the object of the present invention to advance a configuration design and methodology for AB designed NDIR gas sensors such that they can become self-commissioning or in other words capable of automatically maintaining their measurement accuracy indefinitely over time after initial calibration. This invention is achieved via extending the previously disclosed Absorption Biased methodology of U.S. Pat. No. 8,143,581 and Re-calibration methodology without the need of standard gases (U.S. Ser. No. 13/149,738, Wong) for NDIR gas sensors.

SUMMARY OF THE INVENTION

The present invention is generally directed to a self-calibrating NDIR gas sensor and its use in which an infrared source illuminates a signal channel that is longer than a reference channel while electronics are used to calculate a chosen gas concentration in a sample chamber containing the two channels. The difference in length between the two channels creates an absorption bias between outputs of a signal detector and a reference detector, each of the two detectors having an identical narrow band pass filter with the same Center Wavelength ("CWL"), Full Width Half Maximum (FWHM) and transmittance efficiency at the CWL. A second pair of detectors, called standard detectors, are placed in the two channels, and both of these standard detectors have an identical standard narrow band pass filter with the same Center Wavelength ("CWL"), Full Width Half Maximum (FWHM) and transmittance efficiency at the CWL and the CWL of the standard narrow band pass filter is a neutral wavelength. The electronics of the sensor is calibrated by use of a calibration curve generated by using a normalized ratio of the signal channel output to the reference channel output that starts at unity when there is zero concentration of the chosen gas. The calibration curve is self-calibrated by using a stored standard gamma ratio obtained at a first period of time and a measured standard gamma ratio obtained at a second period of time after the first period of time, the standard gamma ratio being the ratio of a standard signal output from a standard signal detector to a standard reference output from a standard reference detector.

Such an NDIR gas sensor can be made to detect a second gas by including a second signal detector and a second reference detector that function similarly to the signal and reference detector, except that they are designed to detect a different gas. This additional pair of detectors will each have an identical second chosen gas narrow band pass filter with the same Center Wavelength ("CWL"), Full Width Half Maximum (FWHM) and transmittance efficiency at the CWL and will have its own calibration curve generated by using a second chosen gas normalized ratio of the second chosen gas signal output to the second chosen gas reference output that starts at unity when there is zero concentration of the second chosen gas. As was the case with a single gas detection sensor, the second gas calibration curve is self-calibrated by using the stored standard gamma ratio and the measured standard gamma ratio.

The NDIR gas sensor can also be recalibrated by comparing the sample concentration of a gas it is detecting to a second gas measurement of such gas determined by a secondary gas standard and then adjusting the normalized ratio of the signal output to the reference output for the gas based upon a reversed calibration curve algorithm that is a non-linear equation if a difference between the sample concentration of the gas and the second gas measurement exceeds a preselected threshold.

Accordingly, it is a primary object of the present invention to provide an NDIR gas sensor that self-calibrates itself.

This and further objects and advantages of the present invention will be apparent to those skilled in the art in connection with the drawings and the detailed description of the invention set forth below.

DETAILED DESCRIPTION OF THE INVENTION

Figure 1:
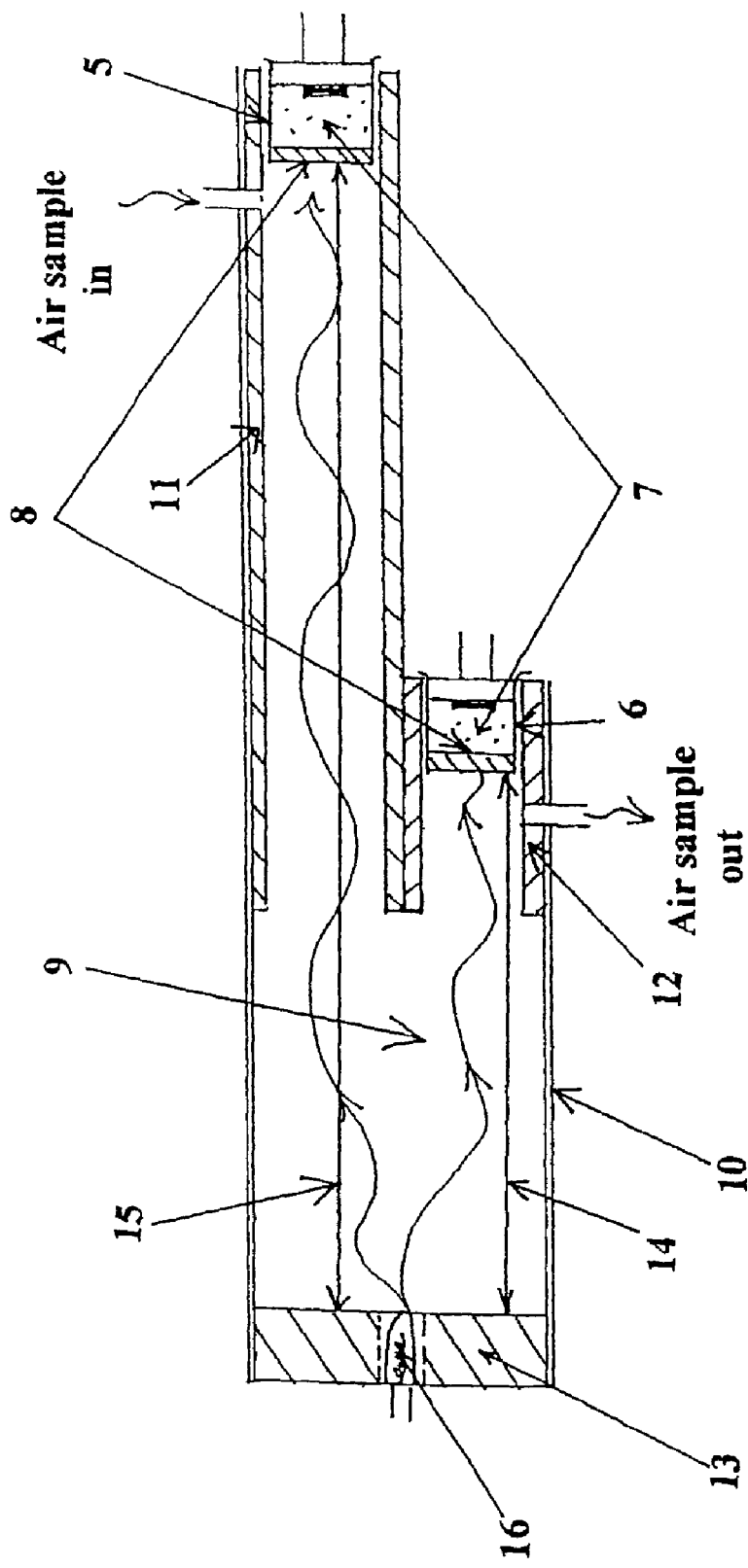
FIG. 1 depicts the optical component layout for an Absorption Biased NDIR gas sensor.

The present invention is an extension of the present author's earlier teaching in advancing an Absorption Biased (AB) methodology for NDIR gas sensors capable of significantly reducing output drifts over time. This AB methodology can be reviewed briefly as follows. First of all, this methodology is based upon a conventional Double Beam Configuration Design for NDIR gas sensors. Two channels or beams are set up, one labeled Signal and the other Reference. Both channels share a common infrared source but have different detectors, each of which is equipped with the same or identical narrow band-pass filter used to spectrally define and detect the target gas of interest. Both detectors for the two channels share the same thermal platform with each other and also with the sample chamber and the common infrared source mount for the sensor. An absorption bias is deliberately established between the Signal and Reference channels by having the sample chamber path length longer for the Signal channel than that for the Reference channel. By so doing, the detector output of the Reference channel is always greater than that of the Signal channel when there is target gas present in the sample chamber. This is due to the fact that there is more absorption taken place in the Signal channel because of its longer sample chamber path length. By applying this absorption bias between the Signal and Reference channels, one is able to calibrate the sensor even when both channel detectors have the same and identical narrow band-pass filters.

Following the conventional NDIR Double Beam design, it is always the ratio value of the Signal channel detector output over the Reference channel detector output that is used to process the different gas concentrations present in the sample chamber. The absorption Biased (AB) methodology for NDIR gas sensors recognized the significance of this zero target gas ratio called "Gamma" that is unrelated to the Physics of this gas measurement technique because there is no gas absorption taken place. By normalizing the ratio of the outputs for the Signal and Reference channels with Gamma and plotting this normalized ratio value as a function of the target gas concentration in the sample chamber to obtain the calibration curve, one is in essence separating the invariant Physics treatment of the NDIR gas sensing principle from the other inevitably changing components treatment of the sensor over time. In other words, any changes in the calibration curve for an AB designed NDIR gas sensor will only be reflected in the changing value of Gamma over time. It will not be reflected in the Physics measurement principle of such an NDIR gas sensor, which is supposed to always remain invariant. If the output of the infrared source for any NDIR gas sensor is changing spectrally over time due to whatever reason, and it is delivered to the Signal and Reference channel detectors, and these detectors have different spectral narrow band-pass filters, this changing spectral output of the source will destroy the invariance of the absorption Physics treatment for the sensor. This is because the ratio of the two channels at the very beginning establishes spectrally the absorption Physics for the gas measurement based upon the spectral output of the source which therefore cannot change over time. Such is actually the case for non-AB designed Double Beam NDIR gas sensors since the Signal and the Reference channel detectors, unlike the AB-designed gas sensors, each has its own and different spectral narrow band-pass filters instead of identical ones. Therefore when the source changes spectrally over time, the ratio of the Signal channel output over the Reference channel output for non-AB designed Double Beam NDIR gas sensors will change causing sensor output drifts over time.

The present author's earlier teaching advancing the Absorption Biased methodology for NDIR gas sensors is indeed one of the appropriate design approaches that will guarantee that even if the spectral content of the infrared source changes over time and is delivered to both the Signal and Reference channel detectors, the invariant Physics measurement principle for the sensor will not be affected. This is because both the Signal and Reference channel detectors are provided with exactly the same spectral filter for the detection of a particular gas, such as, for example, $CO_2$. Also, by knowing the fact that the performance characteristics of infrared detectors are a strong function of their operating temperature and also that their spectral aging characteristics track one another if they are of the same kind, designing the Signal and Reference detectors to be of the same kind and making sure that they share the same thermal platform will further preserve the invariance of the Physics measurement principle for the AB designed NDIR gas sensors over time.

The present invention is a further extension of the author's earlier disclosure in advancing a re-calibration technique for AB designed NDIR gas sensors without the need of standard gases. In that technique, the calibration curve of an AB designed NDIR gas sensor is transformed into a curve that expresses the amount of the target gas present in the sample chamber, P (ppm), as an nth order polynomial of the normalized ratio, R, of the Signal channel detector output over the Reference channel detector output. For a third order polynomial, which is plenty accurate for most applications, this calibration curve transformation can be quantitatively expressed in terms of P (ppm), R and Gamma as follows:

$$P(ppm) = A_0 + A_1 \times R + A_2 \times R^2 + A_3 \times R^3 \quad (1)$$

$$Gamma = V_{S0}/V(\text{zero target gas in sample chamber}) \quad (2)$$

$$R = (V_S/V)/Gamma \quad (3)$$

where $V_S$ and $V_R$ are respectively the Signal and Reference channel detector outputs when there is target gas in the sample chamber. Note that in this transformation of the calibration curve for the sensor, P (ppm) and Gamma of Equations (1) and (2) above represent respectively the invariant Physics principle portion and the inevitably variant components portion of the methodology. But since the parameter R is a function of Gamma [see Equation (3)], when there is a change in the value for Gamma over time and is not corrected, R will be affected and the calibration curve for the sensor will change accordingly leading to sensor output drifts. However, if for whatever reason the change in Gamma over time is known, the value of R can be corrected back to its proper value, and the original calibration curve for the sensor as represented by Equation (1) will still be valid. Under that circumstance, no output drifts should be detected from the sensor and it will stay accurate over time.

In order to achieve a simple, easy and inexpensive re-calibration methodology for AB designed NDIR gas sensors, the expression of P (ppm) as a third order polynomial of R [see Equation (1) above] is reversed into one where R is expressed as a third order polynomial of P (ppm) without changing the value of Gamma as shown below:

$$R = B_0 + B_1 \times P + B_2 \times P^2 + B_3 \times P^3; \text{Gamma unchanged} \quad (4)$$

All AB designed NDIR gas sensors manufactured with the earlier invented re-calibration methodology will carry both polynomials, namely Equation (1) and Equation (4) along with the GAMMA value obtained during initial calibration in their Central Processing Unit (CPU) memory:

Assuming now that an NDIR gas sensor, e.g. $CO_2$, is calibrated with a calibration curve characterized by a third order polynomial with coefficients ($A_0$, $A_1$, $A_2$, $A_3$) and Gamma=$G_0$. As time goes by we recognize that the sensor no longer accurately detects $CO_2$ and we wish to re-calibrate this sensor to its original accuracy or calibration curve. To do this, one has to first prepare a secondary gas standard (in the current example $CO_2$) in the form of a similar NDIR gas sensor which accurately detects and measures the $CO_2$ concentration. This secondary gas standard and the sensor to be re-calibrated are then put in the same still ambience (no winds or air movements within the space) preferably within a space volume of less than 1,000 cu. ft. The objective here is to make sure that both the secondary gas standard and the sensor to be re-calibrated sense or detect the same gas concentration value within this still space. The gas concentration value in the space as measured by the secondary gas standard is now transmitted (via wired or wireless communication) to the sensor to be re-calibrated. Upon receipt of this information, the sensor to be re-calibrated compares this received $CO_2$ concentration value with the one that it meanwhile also measures by determining the value of R and using its stored calibration curve (Equation 1) and its stored Gamma value of $G_0$. If the gas concentration values are found to be within the expected accuracy limit (say +/−25 μm), a signal will be sent back to the secondary gas standard sensor conveying the message that its measurement is good and the unit stays accurately calibrated. However, if the compared values lie outside of the expected accuracy limit, then the unit needs re-calibration and it will attempt to re-calibrate itself automatically as outlined below.

Using the received gas concentration value, it first attempts to calculate the corresponding R value using the stored reverse calibration curve (Equation 4), namely ($B_0$, $B_1$, $B_2$, $B_3$). Using this newly calculated R value, the stored value of $G_0$ and the R value from its own gas measurement earlier that reports the inaccurate gas reading, a new Gamma, $G_N$, can now be determined. By simply replacing the old Gamma=$G_0$ with the newly determined $G_N$ but retaining the original calibration curve [Equation (1)], namely ($A_0$, $A_1$, $A_2$, $A_3$), the sensor has just automatically recalibrated itself.

By carefully reviewing the above described procedures for the successful design of Absorption Biased (AB) NDIR gas sensors and the formulation of a convenient re-calibration technique for AB designed NDIR gas sensors without the need of standard gases, one might recognize that the key concept that makes them possible is the acknowledgement that the calibration curve for these sensors can be separated into two portions, one portion based upon the NDIR gas measurement Physics which is invariant over time and the other portion is based upon the inevitably variant components of the sensors that will change over time. Furthermore, if the sensor is not making any target gas measurement, i.e. when there is no target gas present in the sample chamber, the ratio of the Signal channel detector output ($V_{S0}$) over the Reference channel detector output ($V_{R0}$), which is designated as GAMMA=$V_{S0}/V_{R0}$, belongs uniquely only to the variant components portion of the calibration curve and will change as the component characteristics of the sensor inevitably change over time, for example from aging. By normalizing the ratio of the Signal channel detector output ($V_S$) over the Reference channel detector output ($V_R$) by Gamma, designated as R=($V_S/V_R$)/GAMMA, one can combine the two portions of the calibration curve together to obtain the complete calibration curve for the sensor.

Recognizing the fact that it is only the GAMMA for the sensor that can change over time, the re-calibration methodology for AB designed NDIR gas sensors is simply a procedure that updates the GAMMA of the sensor to be re-calibrated. But as can be seen from above, this re-calibration procedure involving only the GAMMA is still rather complicated requiring first the creation of a common gas concentration level for both the sensor to be re-calibrated and a secondary standard gas sensor. Although the gas concentration level in the common vicinity or neighborhood of the two sensors could be conveniently used as the gas standard, the re-calibration procedure still has to take place physically between the two sensors before the sensor to be re-calibrated could update its GAMMA and thereby recalibrate itself.

Figure 2:
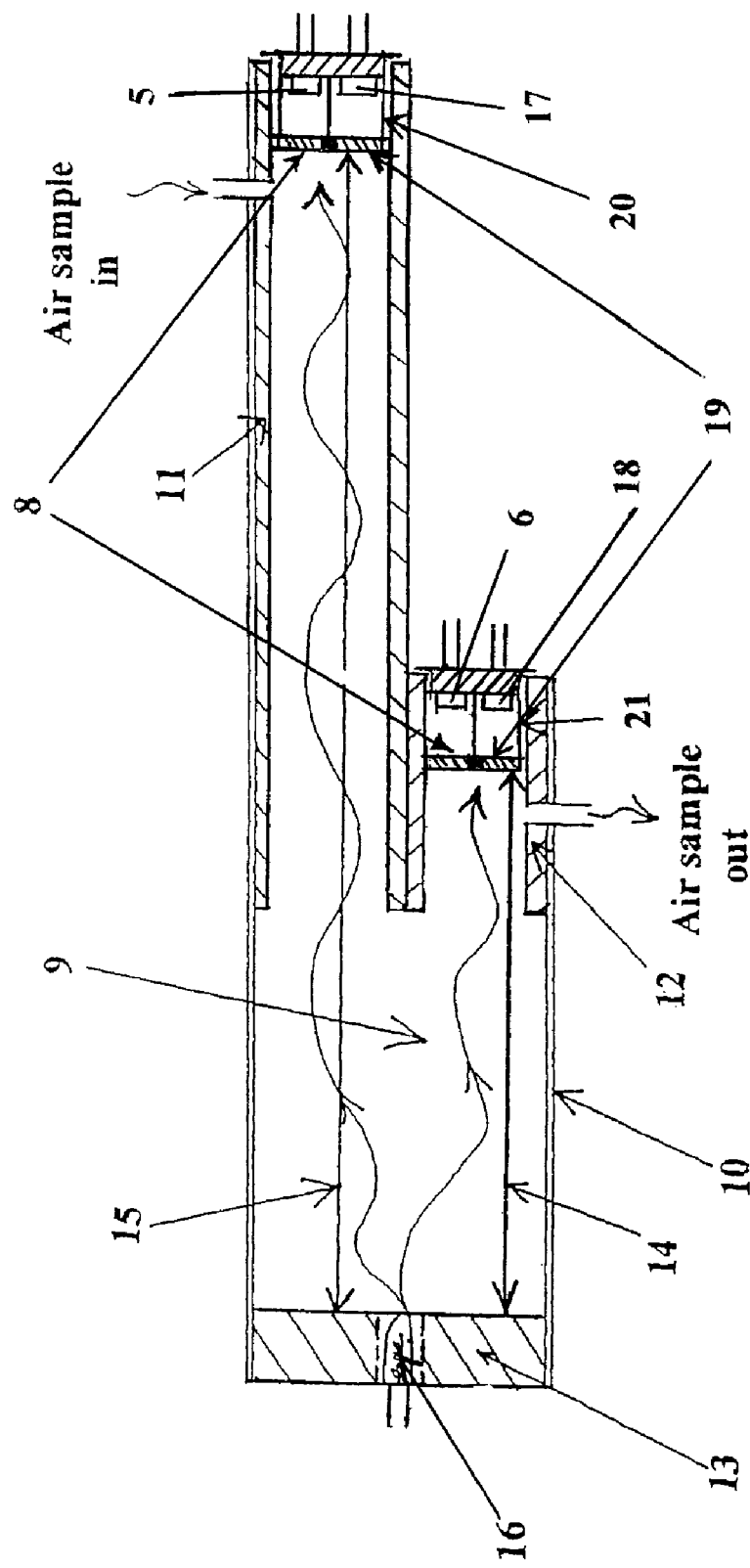
FIG. 2 depicts the optical component layout for a self-commissioning Absorption Biased NDIR gas sensor.

The present invention advances a different methodology to update the GAMMA of an AB designed NDIR gas sensor over time without the need for using a secondary gas standard sensor to carry out a re-calibration procedure. This methodology is described as follows. Using the optical component layout for an Absorption Biased NDIR gas sensor as depicted in FIG. 1 (U.S. application Ser. No. 12/859,749, Wong, filed 21 Aug. 2012), the first step is to install a "Standard" Signal channel detector 17 and a "Standard" Reference detector 18 both equipped with the same and identical band-pass filter 19 neutral to the detection of the target gas respectively next to the Signal channel detector 5 and the Reference channel detector 6 as shown in FIG. 2. As disclosed earlier, both the Signal channel detector 5 and the Reference channel detector 6 are equipped with the same narrow band-pass filter 8 which is used to detect the gas of interest in the sample chamber 9 (see FIGS. 1 and 2). Detectors 5, 6, 17 and 18 are all of the same kind but each has its own spectral filter. Detectors 5 and 6 have the same spectral filter for the detection of the target gas whereas detectors 17 and 18 have the same filter that is neutral to the detection of the target gas, i.e. passing no radiation that would be absorbed by it. As a matter of fact detectors 5 and 6 in the component layout configuration for an AB designed NDIR gas sensor as shown in FIG. 1 are single channel detectors. When detectors 5 and 17 and also detectors 6 and 18 are installed next to each other together as pairs, they could be respectively two dual-channel detectors 20 and 21 (see FIG. 2). The values for the CWL and FWHM for the filter 8 depend upon which target gas the sensor is designed to detect. The CWL for the neutral band-pass filters 19 (see FIG. 2) can be at 2.20µ, 3.91µ or 5.00µ with a FWHM of ~0.1µ. None of the common gases encountered by the general public everyday including those in the atmosphere have absorption bands at these wavelengths within the specified spectral passband of ~0.1µ.

A new sensor parameter called "Standard GAMMA" which is the ratio of the output of the "Standard" Signal channel detector 17 over the output of the "Standard" Reference channel detector 18 (see FIG. 2) is now defined and created. First of all, the value of "Standard GAMMA" is independent of the presence of the target gas in the sample chamber since the spectral filters that the "Standard" detectors carry are neutral to the detection of the target gas. In other words, the radiation passed by these filters will not be absorbed by the target gas in the sample chamber of the sensor. The "Standard GAMMA" is therefore unrelated to the measurement Physics of the AB designed NDIR gas sensor but serves to monitor the performance characteristics of all the sensor components over time. Should there be any change at all in the performance characteristics of the sensor components over time, e.g. due to aging, the value of "Standard GAMMA" will change accordingly. The value of the regular GAMMA of the AB designed NDIR gas sensor will also change when the performance characteristics of the sensor components change over time and hence affecting the calibration curve of the sensor. But the only way to compensate for the change of the GAMMA value in order to restore the measurement accuracy of the sensor is to update it from time to time. This can be done by flowing 100% dry N2 through the sample chamber of the sensor and re-determine the correct GAMMA value or to execute the re-calibration methodology earlier disclosed by the present author (U.S. application Ser. No. 13/149,738, Wong, filed 31 May 2011). The present invention advances a third way to update the value of GAMMA when there are changes in the performance characteristics of the sensor components over time by taking advantage of the definition and creation of the concept for "Standard GAMMA".

As it turns out, since both values of the regular GAMMA and "Standard GAMMA" are affected only by the changes in the performance characteristics of the sensor components over time and are both independent of the measurement Physics of the AB designed NDIR gas sensor, they actually are directly proportional to each other. Because of this fact, any change taking place in the regular GAMMA can be corrected by knowing the change in the value of "Standard GAMMA" over the same period of time. As a matter of fact, by measuring the value of "Standard GAMMA" and storing it along with the initial calibration curve, namely $(A_0, A_1, A_2, A_3)$ [see Equation (1) above] and the regular GAMMA, the "Standard GAMMA" can be used to update the regular GAMMA when the performance characteristics of the sensor components change over time. It can update proportionally the value of the regular GAMMA with the change it detects in itself in order to preserve the measurement accuracy of the sensor going forward in time. In other words, such a sensor has now become self-commissioning, namely knowing how to correct any performance characteristics changes in the sensor components over time thereby restoring the measurement accuracy of the sensor since its initial calibration.

A sensor according to the present invention is ideally suited for use with the HVAC industry, especially when numerous such sensors are networked together in a single structure, such as a building. The accuracy gained by continued self-commissioning allows networked sensors to now fulfill a long-felt need for stable sensors. In addition, multiple sensors can be combined within a single sensor unit, by adding one or more additional pairs of detectors, one of which is in the signal channel, the other of which is in the reference channel, such additional pairs of gas detectors meeting the requirements of an AB designed NDIR gas sensor—namely, that this new pair of detectors is equipped with the same or identical narrow band-pass filter used to spectrally define and detect a different target gas of interest. In other words, just as FIG. 2 illustrates two pairs of detectors, as compared to FIG. 1, such a sensor would now have three detectors in each of the signal and reference channels, two of which function to detect two different target gasses, and one of which serves as the Standard in accordance with the teachings of this invention. Note that a single pair of Standard detectors can be used to calibrate multiple pairs of different target gas detectors. Thus, a single sensor can be used to detect two or more gasses, such as $CO_2$ and water vapor, and the information obtained from the Standard can be used to self-commission the multiple gas detectors contained in the same single sensor.

In summary, the present invention discloses a powerful new NDIR gas sensor that is self-commissioning, that can detect one or more target gases, which can be networked for inclusion in sophisticated networking applications that have gone unused to date for want of suitable sensors. The self-commissioning sensors disclosed herein ensure that such sensors will represent a major advance in the field of NDIR gas sensors.

But, as important as self-commissioning is, it is still possible that sensors according to the present invention may ever so slowly drift over time, albeit in an amount of time much longer than presently encountered within the industry. The reason for this is the lack of a perfect source. The present invention ensures that changes in the intensity or spectral content of the source will be corrected by self-commissioning. Yet, if there is physical change in the source that affects its radiation pattern, which might theoretically occur if, for example, there is sagging of a filament in an incandescent light bulb or possible bubbling on a MEMS source, there is a possibility of a very slight drift over a long period of time that cannot be corrected by self-commissioning. Luckily, however, this theoretical problem can be overcome by also using the re-calibration methodology for AB designed NDIR gas sensors already disclosed in U.S. patent application Ser. No. 13/149,738, and such methodology can be accomplished by use of apparatus disclosed in U.S. patent application Ser. No.

13/348,568, filed Jan. 11, 2012, the disclosure of which is specifically incorporated herein by reference.

So, in conclusion, when a sensor according to the present invention is also equipped to take advantage of re-calibration methodology that uses a calibration master NDIR gas sensor to calculate a master gas concentration which is used to recalibrate the sensor, or multiple master gas concentrations if the sensor is being used to detect multiple gas concentrations, a drift-free sensor is truly obtained which, if it ever does drift, can easily be recalibrated. And, even if the sensor never does drift, its users will know it can quickly be checked and recalibrated if need be. This then represents about as perfect an NDIR sensor as their ever has been, one that can only be improved with respect to drift by use of a perfect source.

The invention has been described herein with reference to certain earlier disclosures by the author presented for illustration and explanation only should not limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A Non-Dispersive Infrared ("NDIR") gas sensor for detecting the presence of a chosen gas, comprising:
   an infrared source for generating infrared radiation into a sample chamber to illuminate a signal channel path length and a reference channel path length, the signal channel path length being longer than the reference channel path length;
   a signal detector located in the signal channel path length;
   a standard signal detector located in the signal channel path length;
   a reference detector located in the reference channel path length;
   a standard reference detector located in the reference channel path length; and
   electronics for determining a sample concentration of the chosen gas;
   wherein each of the signal detector and the reference detector have an identical narrow band pass filter with the same Center Wavelength ("CWL"), Full Width Half Maximum (FWHM) and transmittance efficiency at the CWL;
   wherein each of the standard signal detector and the standard reference detector have an identical standard narrow band pass filter with the same Center Wavelength ("CWL"), Full Width Half Maximum (FWHM) and transmittance efficiency at the CWL and the CWL of the standard narrow band pass filter is a neutral wavelength;
   wherein the electronics determines a sample concentration of the chosen gas in the sample chamber by use of an absorption bias between a signal channel output ("$V_S$") of the signal detector and a reference channel output ("$V_R$") of the reference detector;
   wherein the electronics is calibrated by use of a calibration curve based upon a gamma ratio ("G") that has been normalized by the gamma ratio when no chosen gas is present in the sample chamber ("$G_0$"), G being a ratio of $V_S$ divided by $V_R$; and
   wherein the electronics self-calibrates the calibration curve by using a stored standard gamma ratio obtained at a first period of time and a measured standard gamma ratio obtained at a second period of time after the first period of time, the standard gamma ratio being the ratio of a standard signal output from the standard signal detector to a standard reference output from the standard reference detector.

2. The NDIR gas sensor of claim 1 wherein the calibration curve is self-calibrated by using a ratio of the stored standard gamma ratio to the measured standard gamma ratio to proportionally update $G_0$.

3. The NDIR gas sensor of claim 2 further comprising:
   a second chosen gas signal detector located in the signal channel path length;
   a second chosen gas reference detector located in the reference channel path length; and
   electronics for determining a second sample concentration of a second chosen gas;
   wherein each of the second chosen gas signal detector and the second chosen gas reference detector have an identical second chosen gas narrow band pass filter with the same Center Wavelength ("CWL"), Full Width Half Maximum (FWHM) and transmittance efficiency at the CWL;
   wherein the electronics for determining a second sample concentration of the second chosen gas in the sample chamber by use of a second absorption bias between a second chosen gas signal channel output ("$V_{S2}$") of the second chosen gas signal detector and a second chosen gas reference channel output ("$V_{R2}$") of the second chosen gas reference detector; and
   wherein the electronics for determining the second sample concentration of the second chosen gas is calibrated by use of a second calibration curve based upon a second gamma ratio ("$G_2$") that has been normalized by the second gamma ratio when no second chosen gas is present in the sample chamber ("$G_{02}$"), $G_2$ being a ratio of $V_{S2}$ divided by $V_{R2}$.

4. The NDIR gas sensor of claim 3 wherein the second calibration curve is self-calibrated by using the ratio of the stored standard gamma ratio to the measured standard gamma ratio to proportionally update $G_{02}$.

5. The NDIR gas sensor of claim 4 further comprising:
   recalibration electronics for recalibrating the NDIR gas sensor by comparing the sample concentration of the chosen gas to a second gas concentration of the chosen gas determined by a secondary gas standard and adjusting $G_0$ based upon a reversed calibration curve algorithm that is a non-linear equation if a difference between the sample concentration of the chosen gas and the second gas concentration exceeds a preselected threshold; and
   second recalibration electronics for recalibrating the NDIR gas sensor by comparing the sample concentration of the second chosen gas to a second gas concentration of the second chosen gas determined by a second chosen gas secondary gas standard and adjusting $G_{02}$ based upon a second reversed calibration curve algorithm that is a non-linear equation if a difference between the sample concentration of the second chosen gas and the second gas concentration of the second chosen gas exceeds a second preselected threshold.

6. The NDIR gas sensor of claim 5 wherein both the recalibration electronics and the second recalibration electronics are performed by a single processor configured to execute one or more computer program modules.

7. The NDIR gas sensor of claim 1 further comprising recalibration electronics for recalibrating the NDIR gas sensor by comparing the sample concentration of the chosen gas to a second gas concentration of the chosen gas determined by a secondary gas standard and adjusting the normalized ratio of the signal output to the reference output based upon a reversed calibration curve algorithm that is a non-linear equation if a difference between the sample concentration of the chosen gas and the second gas concentration exceeds a preselected threshold.

8. A process for determining a sample concentration of a sample gas in a sample chamber of a Non-Dispersive Infrared ("NDIR") gas sensor, comprising:

using a calibration curve to calibrate electronics in the NDIR gas sensor, said calibration curve being based upon a gamma ratio. ("G") that has been normalized by the gamma ratio when no sample gas is present in the sample chamber ("$G_0$"), G being a ratio of a signal channel output ("$V_S$") of a signal channel detector and a reference channel output ("$V_R$") of a reference channel detector;

using a stored standard gamma ratio obtained at a first period of time and a measured standard gamma ratio obtained at a second period of time after the first period of time to determine if the calibration curve needs a calibration correction and, if a correction is needed, making the correction, the standard gamma ratio being a ratio of a standard signal channel output of a standard signal channel detector and a standard reference channel output of a standard reference channel detector;

emitting infrared radiation from an infrared source into the sample chamber, said sample chamber having both a signal channel path length and a reference channel path length, the signal channel path length being longer than the reference channel path length; and using the electronics to determine the sample concentration by use of an absorption bias created between $V_S$ and $V_R$;

wherein the signal channel detector and the reference channel detector have an identical narrow band pass filter with the same Center Wavelength ("CWL"), Full Width Half Maximum (FWHM) and transmittance efficiency at the CWL; and wherein the standard signal channel detector and the standard reference channel detector have an identical reference narrow band pass filter with the same Center Wavelength ("CWL"), Full Width Half Maximum (FWHM) and transmittance efficiency at the CWL and the CWL of the reference narrow band pass filter is a neutral wavelength.

9. The process of claim 8 wherein the signal channel path length is comprised of a signal channel waveguide and the reference channel path length is comprised of a reference channel waveguide.

10. The process of claim 9 wherein the signal channel waveguide does not contain a light path within the reference channel waveguide.

11. The process of claim 10 wherein the signal channel waveguide is parallel to the reference channel waveguide.

12. The process of claim 8 wherein the calibration curve is self-calibrated by using a ratio of the stored standard gamma ratio to the measured standard gamma ratio to proportionally update $G_0$.

13. A method useful with a dual-beam non-dispersive infrared ("NDIR") gas sensor having a sample chamber used to detect a sample gas, comprising:

using a calibration curve of the NDIR gas sensor to calculate a concentration of the sample gas in the sample chamber of the NDIR gas sensor; and recalibrating the NDIR gas sensor to create a recalibrated gas sensor by using a stored standard gamma ratio and a measured standard gamma ratio and a self-calibration algorithm to correct the calibration curve for a difference between the stored standard gamma ratio and the measured standard gamma ratio when the difference exceeds a preselected threshold;

wherein the stored standard gamma ratio is obtained at a first period of time and the measured standard gamma ratio is obtained at a second period of time after the first period of time, the gamma ratio being the ratio of signal to reference outputs from a standard signal channel detector located in a signal channel path length and a standard reference channel detector located in a reference channel path length;

wherein the standard signal channel detector and the standard reference channel detector have an identical reference narrow band pass filter with the same Center Wavelength ("CWL"), Full Width Half Maximum (FWHM) and transmittance efficiency at the CWL and the CWL of the reference narrow band pass filter is a neutral wavelength; and wherein the calibration curve is based upon a combination of a physics measurement component of the NDIR gas sensor and a sensor measurement component of the NDIR gas sensor.

14. The method of claim 13 wherein the NDIR gas sensor uses an identical spectral narrow band pass filter for wavelength selection for both a signal channel having a signal channel pathlength and a reference channel having a reference channel pathlength and an absorption bias is applied to the signal channel by making the signal channel path length longer than the reference channel pathlength.

15. The method of claim 14 wherein the calibration curve is based upon a gamma ratio ("G") that has been normalized by the gamma ratio when no sample gas is present in the sample chamber ("$G_0$"), G being a ratio of a signal channel output ("$V_S$") of the NDIR gas sensor divided by a reference channel output ("$V_R$") of the NDIR gas sensor.

16. The method of claim 15 wherein the NDIR gas sensor has no moving parts for effecting the interposition of a plurality of spectral filters or an absorbing cell or a non-absorbing cell to create both a signal channel and a reference channel.

17. The method of claim 16 further comprising recalibrating the NDIR gas sensor by comparing the concentration of the sample gas ("P") to a second gas concentration of the sample gas determined by a master NDIR gas sensor and adjusting $G_0$ based upon a reversed calibration curve algorithm that is a non-linear equation if a difference between P and the second gas concentration exceeds a preselected threshold.

18. In a dual-beam non-dispersive infrared ("NDIR") gas sensor having a sample chamber used to detect a sample gas through use of electronics that receives a signal channel output ("$V_S$") from a signal channel detector and a reference channel output ("$V_R$") from a reference channel detector, the improvement, comprising:

electronics for calculating a gas concentration ("P") of the sample gas detected by the NDIR gas sensor through use of a calibration curve for the NDIR gas sensor, said calibration curve being obtained from a gamma ratio ("G") that has been normalized by the gamma ratio when no sample gas is present in the sample chamber ("$G_0$"), G being the ratio of $V_S$ divided by $V_R$; and recalibration electronics for recalibrating the NDIR gas sensor by comparing a stored standard gamma ratio to a measured standard gamma ratio determined at a later period of time and adjusting $G_0$ based upon a self-calibration algorithm;

wherein the stored standard gamma ratio is obtained at a first period of time and the measured standard gamma ratio is obtained at a second period of time after the first period of time, the gamma ratio being the ratio of signal to reference outputs from a standard signal channel detector located in a signal channel path length and a standard reference channel detector located in a reference channel path length;

wherein the signal channel detector and the reference channel detector have an identical narrow band pass filter with the same Center Wavelength ("CWL"), Full Width Half Maximum (FWHM) and transmittance efficiency at the CWL; and wherein the standard reference detector and the standard signal detector have an identical reference narrow band pass filter with the same Center Wavelength ("CWL"), Full Width Half Maximum (FWHM) and transmittance efficiency at the CWL and the CWL of the reference narrow band pass filter is a neutral wavelength.

19. The dual-beam NDIR gas sensor of claim 18 wherein the NDIR gas sensor has no moving parts for effecting the interposition of a plurality of spectral filters or an absorbing cell or a non-absorbing cell to create both the signal channel and the reference channel.

20. The dual-bean NDIR gas sensor of claim 19 wherein the NDIR gas sensor is linked to a network that connects it to a plurality of other NDIR gas sensors.

* * * * *